(12) United States Patent
Gabel et al.

(10) Patent No.: US 6,419,955 B1
(45) Date of Patent: Jul. 16, 2002

(54) PROCESS FOR MAKING BISPHOSPHONATE COMPOSITIONS

(75) Inventors: Rolf-Dieter Gabel, Schwetzingen; Jörn Möckel, Dossenheim; Heinrich Woog, Laudenbach, all of (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/413,989

(22) Filed: Oct. 7, 1999

(30) Foreign Application Priority Data

Oct. 9, 1998 (EP) .............................................. 98119103

(51) Int. Cl.$^7$ ................................................. A61K 9/46
(52) U.S. Cl. ....................... 424/466; 424/400; 424/451; 424/464; 424/499; 424/501
(58) Field of Search ................................ 424/466, 451, 424/497

(56) References Cited

U.S. PATENT DOCUMENTS

| | | |
|---|---|---|
| 4,624,947 A | 11/1986 | Blum et al. |
| 4,711,880 A | 12/1987 | Stahl et al. |
| 4,800,087 A * | 1/1989 | Mehta .......................... 424/497 |
| 4,927,814 A | 5/1990 | Gall et al. |
| 4,939,130 A | 7/1990 | Jaeggi et al. |
| 4,946,654 A * | 8/1990 | Uhlemann et al. .......... 422/140 |
| 4,980,171 A | 12/1990 | Fels et al. |
| 5,358,941 A | 10/1994 | Bechard et al. |
| 5,525,354 A * | 6/1996 | Posti et al. .................. 424/451 |
| 5,681,590 A | 10/1997 | Bechard et al. |
| 5,882,656 A | 3/1999 | Bechard et al. |

FOREIGN PATENT DOCUMENTS

| | | | |
|---|---|---|---|
| EP | 0 275 468 | 7/1988 | |
| EP | 0 583 470 | 2/1994 | |
| WO | WO 93/09785 | 5/1993 | |
| WO | WO 94/12200 | 6/1994 | |
| WO | WO 95/29679 * | 11/1995 | .......... A61K/31/66 |
| WO | WO 96/39150 | 12/1996 | |
| WO | WO 96/41618 | 12/1996 | |

OTHER PUBLICATIONS

Lieberman, et al., Pharmaceutical Dosage Forms:2$^{nd}$ Ed, Marcel Dekker, Inc., New York and Basel, pp. 1–76 (1990).
W. Pietsch, Size Enlargement by Agglomeration, John Wiley & Sons, Chichester, pp. 200–201, 394–399.
Remington's Pharmaceutical Sciences, Mack Printing Company, Easton, PA pp. 1604–1615 (1985).

* cited by examiner

Primary Examiner—Thurman K. Page
Assistant Examiner—Robert M. Joynes
(74) Attorney, Agent, or Firm—George W. Johnston; Dennis P. Tramaloni; F. Aaron Dubberley

(57) ABSTRACT

The present invention relates to a process for the preparation of bisphonate-containing pharmaceutical compositions for oral administration wherein the active substance is wet-granulated in a fluidized-bed granulator and the wet granulate is dried in the fluidised bed granulator. The dried granulate is further processed to produce desired dosage forms.

8 Claims, No Drawings

PROCESS FOR MAKING BISPHOSPHONATE COMPOSITIONS

BACKGROUND OF THE INVENTION

The invention relates to a process for the preparation of oral-application pharmaceutical compositions containing as the active substance aminoalkyl-1,1-diphosphonic acid derivatives, free acids, pharmaceutically compatible salts or hydrates thereof (hereinafter called by the general term bisphosphonates).

Bisphosphonates are important in the treatment of bone diseases and some disturbances of calcium metabolism such as hypercalcaemia, osteoporosis, tumour osteolysis, Paget's disease, etc.

Pharmaceutical preparations in general have to satisfy exacting requirements regarding content, uniformity of content and purity. Special properties of active substances may adversely influence the content, uniformity and purity of the form of administration. It is known that bisphosphonates are a group of substances with a strong tendency to form complexes with polyvalent metal ions. Conventional pharmaceutical preparations for oral application are usually produced in installations and apparatus with metal surfaces, and consequently when bisphosphonates are processed the highly complex-forming active substance comes into contact with complexable material. This is particularly the case when water or aqueous media are used in processing. One remedy is dry processing, particularly on the direct tableting principle, since wet granulation is avoided in that case. Direct tableting is a very suitable method for producing high-dosage tablets. As is known, however, high-dosage forms of bisphosphonates for oral administration are particularly subject to compatibility problems, which makes oral treatment difficult. Aminodiphosphonic acids in particular cause irritation of the upper gastrointestinal tract (H. Fleisch, Bisphosphonates in Bone Disease, Herbert Fleisch, Berne, 1993; pages 126–131). In direct tableting furthermore, as in the case when non-granulated powder is filled into gelatine capsules, there is a risk of fluctuations in content, particularly for low or very low-dosage active substances. For this reason wet granulation is indispensable, in spite of the said risk of complex-forming. When high-speed mixers are used, the active substance is mixed with adjuvants and is granulated wet with water or aqueous binder solution. In the process the active substance is brought into very intensive contact with the metal surfaces of the apparatus. The risk of complex-forming can be additionally increased by the abrasive effect of some pharmaceutical adjuvants.

SUMMARY OF THE INVENTION

The object of the invention therefore is to develop a process for the preparation of bisphosphonate-containing pharmaceutical compositions for oral application, preferably containing up to 50 mg of active substance per unit dose, so as to reduce the loss of active substance in the preparation of the compositions.

To this end, according to the invention, bisphosphonates are converted by known fluidised-bed granulation (Liebermann et al. "Pharmaceutical Dosage Forms": Tablets, $2^{nd}$ Ed. 1990, Marcel Dekker, New York, Basle; Pietsch: "Size Enlargement by Agglomeration", John Wiley & Sons, Chichester) into formulations suitable for oral application. Fluidised-bed granulation is a conventional method of wet granulation. Unexpectedly, however, this method can reduce the loss of active substance or the diminution in content of active substance in the formulation to less than 6% by weight, preferably less than 4% by weight.

The invention thus relates to a process for the preparation of pharmaceutical compositions for the oral application of bisphosphonates, wherein the bisphosphonate is wet-granulated in manner known per se in a fluidised-bed granulator with adjuvants and wherein the wet granulate is then dried in the fluidised-bed granulator, screened through a screen having a suitable mesh width and further processed by techniques known per se to form pharmaceutical compositions for oral administration to a patient in unit dosage form.

DETAILED DESCRIPTION OF THE INVENTION

The said disadvantage of complex-forming during wet granulation, therefore, is no longer a problem when preparing low-dosage bisphosphonate preparations. The pharmaceutical compositions are preferably produced with a content of from about 0.1 to 50 mg, particularly from about 0.1 to 10 mg bisphosphonate per unit dose. The term "unit dose" denotes the discrete form of administration, e.g. the individual tablet or capsule.

The pharmaceutical compositions are prepared according to the invention by wet granulation, i.e., granulating the active substance in the presence of water in a fluidised-bed granulator known per se. The pharmaceutical compositions of the present invention can be formulated using adjuvants which have no abrasive effect during processing in conventional pharmaceutical production plants, e.g. as in the case of silicon dioxide.

In accordance with the present invention, any conventional method of wet granulation may be utilized. Preferably, in carrying out the wet granulation, the active substance in solution or suspension together with an aqueous binder solution is sprayed onto other suitable adjuvants and granulated. This embodiment of the present invention is especially preferred for the preparation of compositions containing 0.1 to 5 mg of active substance. In another embodiment of the present invention, the active substance and adjuvants in dry powder form are placed in a fluidised-bed granulator and granulated by spraying aqueous binder solution into the powder mixture. This embodiment is especially preferred for the preparation of compositions containing 10 to 50 mg of active substance. In still another embodiment, water may also be sprayed into the powder mixture, which in this case contains a binder.

The resulting wet granulate is then dried in the fluidised-bed granulator until the material has an acceptable residual moisture content for further processing to a pharmaceutical composition in other machines. The dried granulate is passed through a screen having a suitable mesh width and then further processed by known techniques, being mixed with other additives if required.

The following bisphosphonates are active substances which can be used according to the invention in the form of free acids or pharmaceutically compatible salts or hydrates, particularly sodium salts:

(4-amino-1-hydroxybutylidene)bis-phosphonate (alendronate), (Dichloromethylene)bis-phosphonate (clodronate),

[1-hydroxy-3-(1-pyrrolidinyl)-propylidene]bis-phosphonate (EB-1053), (1-hydroxyethylidene)bis-phosphonate (etidronate),

[1-hydroxy-3-(methyl pentyl amino)propylidene]bis-phosphonate (ibandronate),

[Cycloheptylamino)-methylene]bis-phosphonate (incadronate), (6-amino-1-hydroxyhexylidene)bis-phosphonate (neridronate),

[3-(dimethylamino)-1-hydroxypropylidene]bis-phosphonate (olpadronate), (3-amino-1-hydroxypropylidene)bis-phosphonate (pamidronate),

[1-hydroxy-2-(3-pyridinyl)ethylene]bis-phosphonate (risedronate),

[[(4-chlorophenyl)thiol]-methylene]bis-phosphonate (tiludronate),

[1-hydroxy-2-imidazo-(1,2-a)pyridin-3-yl ethylidene]bis-phosphonate (YH 529),

[1-hydroxy-2-(1H-imidazol-1-yl)ethylidene]bis-phosphonate (zoledronate).

The said substances and their preparation are known and described, for example, in the following references:

U.S. Pat. No. 4,705,651 (Alendronate), U.S. Pat. No. 4,927,814 (Ibandronate), U.S. Pat. Nos. 3,468,935, 3,400,147, 3,475,486 (Etidronate), O. T. Quimby et al, J. Org. Chem. 32, 4111 (1967) (Clodronate) and U.S. Pat. No. 4,505,321 (Risedronate) and U.S. Pat. Nos. 4,134,969 and 3,962,432 (Pamidronate), U.S. Pat. No. 5,130,304 (EB-1053), U.S. Pat. No. 4,970,335 (Incadronate), Belgian Pat. No. 885139 (Neridronate), U.S. Pat. No. 4,054,598 (Olpadronate), U.S. Pat. Nos. 4,746,654, 4,876,248 and 4,980,171 (Tiludronate), U.S. Pat. No. 4,990,503 (YH 529) and U.S. Pat. No. 4,939,130 (Zoledronate).

The invention is preferably used for producing pharmaceutical preparations which contain the active substance in a proportion of from about 0.1 to 50 mg per unit dose, preferably 0.1 to 10 mg, particularly preferably 0.1 to 5 mg and 0.1 to 2.5 mg. Ibandronate is a particularly preferred active substance, particularly in the form of Na-Ibandronate monohydrate.

The nonabrasive adjuvants, i.e., adjuvants which do not have an abrasive effect during granulation may, according to the invention, be fillers such as lactose in hydrate or anhydrate form, sugar alcohols such as mannitol; tableting adjuvants such as cellulose in microcrystalline or fibrous form; and binders such as polyvinyl pyrrolidone (Povidone USP) or cellulose ethers such as methyl hydroxypropyl cellulose. At least one adjuvant is used which acts as binder.

Preferably at least one of the adjuvants is lactose, microcrystalline cellulose or polyvinyl pyrrolidone. In a preferred embodiment 1–99% by weight lactose, 1–99% by weight microcrystalline cellulose, and 0.1–20% by weight polyvinyl pyrrolidone are used, particularly preferably 25–75% by weight lactose, 10–20% by weight microcrystalline cellulose, and 2–3% by weight polyvinyl pyrrolidone.

The granulate is further processed by known methods, using additional adjuvants if required, into desired unit dosage forms, for example, tablets, chewing tablets, effervescent tablets, film tablets, dragees and pellets or filled into hard gelatine capsules or sachets. Tablets so prepared may be coated with conventional films such as described, e.g., in WO 97/39755. The adjuvants used in further processing are conventional lubricants, e.g., stearic acid, disintegrants, e.g., cross-linked polyvinyl pyrrolidone (Crospovidone USPNF), flow-regulators, e.g., colloidal silicon dioxide, tableting adjuvants etc. In one preferred embodiment the further processing of the granulate is carried out with the addition of stearic acid as lubricant in quantities of less than 5% by weight referred to the total weight of the form of administration, particularly 0.05 to 3% by weight of stearic acid.

Preparation of pharmaceutical compositions according to the invention by fluidised-bed granulation, particularly by the drying process in the fluidised-bed granulator, results in less intensive contact between the material and the surface of the apparatus, thus surprisingly reducing the loss of active substance. This is particularly advantageous when the active substance content of the unit dose is small. This substantially avoids the above-described disadvantages in the conventional production of forms for oral administration. Moreover, where the composition is formulated by wet granulation and dried in the fluidised-bed granulator, the process of the present invention can be carried out such that any adjuvants can be used. Therefore, a disadvantage overcome by the present invention is that there is no need to utilize abrasive adjuvants which are commonly used in making bisphosphonate compositions. Thus, by utilizing the process of this invention, the oral bisphosphonate compositions can be formulated with nonabrasive adjuvants thereby reducing the loss of active substance.

The invention will now be explained in further detail with reference to examples, without being limited thereto.

EXAMPLE 1 (COMPARATIVE EXAMPLE)

Production of ibandronate 2.5 mg capsules after granulation in a high-speed mixer/granulator (batch size for 45,000 capsules).

| Constituents | g |
| --- | --- |
| Na-Ibandronate | 120.24 |
| Lactose | 7934.76 |
| Polyvinyl pyrrolidone | 202.50 |
| Polyvinyl pyrrolidone, cross-linked (disintegrant) | 562.50 |
| Stearic acid (lubricant) | 180.00 |

The amount of active substance per capsule is equivalent to 2.5 mg of free acid.

Lactose, ibandronate and polyvinyl pyrrolidone were mixed for 2 minutes at a fill factor of 50% in a high-speed mixer/granulator (Diosna type) and then granulated with water for 8 minutes. The wet granulate was dried in a fluidised bed (Aeromatic-type apparatus), passed through an 0.8 mm screen, mixed with disintegrant and lubricant (Rhoenrad-type mixer, mixing time 10 minutes) and encapsulated in size-2 hard gelatine capsules without compression in a capsule machine (type MG2/G36) having a capacity of 20,000 capsules per hour.

| | |
| --- | --- |
| Set weight of filling: | 200.0 mg |
| Actual weight of filling according to in-process control: | 200.9 mg |

Content of active substance found in capsules produced in this way:

94.8%±5.2% (n=10 individual measurements).

EXAMPLE 2 (COMPARATIVE EXAMPLE)

Production of ibandronate 1.0 mg capsules after granulation in a high-speed mixer/granulator (batch size for 5000 capsules).

| Constituents | g |
| --- | --- |
| Na-Ibandronate | 5.345 |
| Lactose | 999.655 |
| Polyvinyl pyrrolidone | 22.500 |
| Polyvinyl pyrrolidone, cross-linked (disintegrant) | 62.500 |
| Stearic acid (lubricant) | 10.000 |

The amount of active substance per capsule is equivalent to 1.0 mg of free acid.

Lactose, ibandronate and polyvinyl pyrrolidone were mixed for 2 minutes in a high-speed mixer/granulator (Diosna type) and then granulated with water for 10 minutes. The wet granulate was dried in a fluidised bed (Aeromatic-type apparatus), screened through an 0.8 mm screen, mixed with disintegrant and lubricant (Rhoenrad-type mixer, mixing time 10 minutes) and enclosed in size-2 hard gelatine capsules in a capsule machine (type KFM Harro Höfliger).

| Set weight of filling: | 220.00 mg |
| --- | --- |
| Actual weight of filling according to in-process control: | 220.05 mg |

Content of active substance found in the capsules produced in this way:
94.9%±1.9%
(n=10 individual measurements)

EXAMPLE 3

Production of ibandronate 1.0 mg tablets after granulation in a fluidised bed (batch size for 60,000 tablets).

| Constituents | g |
| --- | --- |
| Na-Ibandronate | 64.14 |
| Lactose | 4405.86 |
| Polyvinyl pyrrolidone | 150.00 |
| Polyvinyl pyrrolidone, cross-linked (disintegrant) | 300.00 |
| Stearic acid (lubricant) | 120.00 |
| Microcrystalline cellulose | 900.00 |
| Colloidal SiO$_2$ (flow agent) | 60.0 |

The amount of active substance per tablet is equivalent to 1.0 mg of free acid.

Lactose and 600 g microcrystalline cellulose were granulated with an aqueous solution of polyvinyl pyrrolidone and ibandronate in a fluidised-bed granulator (Aeromatic type). The wet granulate was dried in the fluidised bed (Aeromatic type), passed through a 1.0 mm screen, mixed with disintegrant, lubricant, flow-regulator and 300 g microcrystalline cellulose (Turbula-type mixer, mixing time 5 minutes) and converted into tablets in a tableting press (Korsch type) having a capacity of 25,000 tablets per hour.

| Set weight of tablets: | 100.0 mg |
| --- | --- |
| Actual weight of tablets according to in-process control: | 101.3 mg |

Content of active substance found per tablet produced in this way: 98.3% ±4.2% (n=10 individual measurements).

The active substance content of the tablets was within the acceptance limits.

EXAMPLE 4

Production of ibandronate 0.1 mg tablets after granulation in a fluidised bed (batch size for 150,000 tablets).

| Constituents | g |
| --- | --- |
| Na-Ibandronate monohydrate | 16.95 |
| Lactose | 11158.05 |
| Polyvinyl pyrrolidone | 375.00 |
| Polyvinyl pyrrolidone, cross-linked (disintegrant) | 750.00 |
| Stearic acid (lubricant) | 300.00 |
| Microcrystalline cellulose | 2250.00 |
| Colloidal SiO$_2$ (flow agent) | 150.00 |

The amount of active substance per tablet is equivalent to 0.1 mg of free acid.

Lactose and 1500 g microcrystalline cellulose were granulated with an aqueous solution of polyvinyl pyrrolidone and ibandronate in a fluidised-bed granulator (Aeromatic type). The wet granulate was dried in the fluidised bed (Aeromatic type), passed through a 1.0 mm screen, mixed with disintegrant, lubricant, flow-regulator and 750 g microcrystalline cellulose (Turbula-type mixer, mixing time 10 minutes) and converted into tablets in a tableting press (Korsch type) having a capacity of 60,000 tablets per hour.

| Set weight of tablets: | 100.0 mg |
| --- | --- |
| Actual weight of tablets according to in-process control: | 101.3 mg |

Content of active substance found per tablet produced in this way: 98.5% ±2.4% (n=10 individual measurements).

The active substance content of the tablets was within the acceptance limits.

EXAMPLE 5

Production of ibandronate 2.5 mg film coated tablets after granulation in a fluidised bed

| Constituents | mg/film coated tablet |
| --- | --- |
| Na-Ibandronate, monohydrate | 2.813 |
| Lactose monohydrate | 71.687 |
| Polyvinyl pyrrolidone | 2.500 |
| Microcrystalline cellulose | 15.000 |
| Polyvinyl pyrrolidone, cross-linked (disintegrant) | 5.000 |
| Stearic acid (lubricant) | 2.000 |
| Colloidal SiO$_2$ (flow regulating agent) | 1.000 |
| Core weight | 100.000 |
| Filmcoating suspension (dry material) | 4.000 |
| Weight of film coated tablet | 104.000 |

The amount of active substance per tablet is equivalent to 2.5 mg of free acid.

Lactose and a part (⅔) of the microcrystalline cellulose were granulated with an aqueous solution of polyvinyl pyrrolidone and ibandronate in a fluidised-bed granulator (Aeromatic type). The wet granulate was dried in the fluidised bed (Aeromatic type), passed through a screen, mixed with disintegrant, lubricant, flow-regulator and the rest of the microcrystalline cellulose and converted into tablets in a tableting press.

EXAMPLE 6

Production of ibandronate 20 mg film coated tablets after granulation in a fluidised bed

| Constituents | mg/film coated tablet |
|---|---|
| Na-Ibandronate, monohydrate | 22.500 |
| Lactose monohydrate | 52.000 |
| Polyvinyl pyrrolidone | 2.500 |
| Microcrystalline cellulose | 15.000 |
| Polyvinyl pyrrolidone, cross-linked (disintegrant) | 5.000 |
| Stearic acid (lubricant) | 2.000 |
| Colloidal SiO$_2$ (flow regulating agent) | 1.000 |
| Core weight | 100.000 |
| Filmcoating suspension (dry material) | 4.000 |
| Weight of film coated tablet | 104.000 |

The amount of active substance per tablet is equivalent to 20 mg of free acid.

Lactose, a part (⅔) of the microcrystalline cellulose and ibandronate were granulated with an aqueous solution of polyvinyl pyrrolidone in a fluidised-bed granulator (Aeromatic type). The wet granulate was dried in the fluidised bed (Aeromatic type), passed through a screen, mixed with disintegrant, lubricant, flow-regulator and the rest of the microcrystalline cellulose and converted into tablets in a tableting press.

What is claimed is:

1. A process for preparing an ibandronate-containing pharmaceutical composition in unit dosage form, said composition containing up to 50 mg of ibandronate per unit dose, comprising granulating the ibandronate in the presence of water in a fluidised-bed granulator with adjuvants to form a granulate; drying the granulate in the fluidised-bed granulator; and processing the granulate to produce the pharmaceutical composition in unit dosage form, wherein the adjuvants comprise lactose in an amount of from about 25 to about 75% by weight of the composition, microcrystalline cellulose in an amount of from about 10 to about 20% by weight of the composition, and polyvinyl pyrrolidone in an amount of from about 2 to about 3% by weight of the composition.

2. The process according to claim 1, wherein the ibandronate and the polyvinyl pyrrolidone are granulated in the fluidised be granulator by spraying water into the mixture.

3. The process according to claim 1, wherein the ibandronate in solution or suspension together with an aqueous polyvinyl pyrrolidone solution is sprayed onto the other adjuvants and granulated.

4. The process according to claim 1, wherein the ibandronate is granulated in a fluidised bed granulator by spraying an aqueous polyvinyl pyrrolidone solution into the ibandronate and the other adjuvants.

5. The process according to claim 1, wherein the dosage form is selected from the group consisting of tablets, capsules, film tablets, dragees, pellets, effervescent tablets, chewing tablets and granulates in sachets.

6. The process according to claim 1, wherein the processing step further comprises adding stearic acid to the granulate in an amount of from about 0.05 to about 3% by weight of the composition.

7. The process according to claim 1, wherein the unit dosage form contains from about 0.1 to about 50 mg of the active substance.

8. The process according to claim 4, wherein the unit dosage form contains from about 0.1 to about 5 mg of the active substance.

* * * * *